United States Patent [19]

Lamsa

[11] Patent Number: 4,866,174

[45] Date of Patent: Sep. 12, 1989

[54] METHOD FOR THE PREPARATION OF A THERAPEUTICALLY ACTIVE COMPOUND

[75] Inventor: Jyrki Lamsa, Oulu, Finland

[73] Assignee: Farmos-Yhtyma Oy, Turku, Finland

[21] Appl. No.: 72,725

[22] Filed: Jul. 13, 1987

[30] Foreign Application Priority Data

Oct. 7, 1986 [FI] Finland ................................ 864046

[51] Int. Cl.$^4$ ............... C07D 401/04; C07D 239/48
[52] U.S. Cl. ................................................ 544/323
[58] Field of Search ................................ 544/323, 324

[56] References Cited

U.S. PATENT DOCUMENTS

| 3,644,364 | 2/1972 | Anthony | 544/323 |
| 3,998,827 | 12/1976 | Thomas, Jr. et al. | 544/323 |
| 4,483,781 | 11/1984 | Hartman | 252/95 |

FOREIGN PATENT DOCUMENTS

| 0027693 | 1/1980 | European Pat. Off. | 252/92 |
| 2032434 | 5/1980 | United Kingdom | 544/323 |

OTHER PUBLICATIONS

Chemical Abstracts, vol. 95, No. 23, Abstract 203,982f, 687, Dec. 7, 1981.

Primary Examiner—Mary C. Lee
Assistant Examiner—Z. Northington
Attorney, Agent, or Firm—Burns, Doane, Swecker & Mathis

[57] ABSTRACT

A method for the preparation of 2,4-diamino-3-oxy-6-piperidyl-pyrimidine or minoxidil wherein a compound of the formula

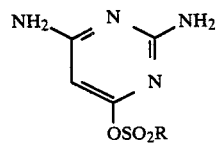

wherein R is a $C_{1-4}$ alkyl or a phenyl group optionally having up to three $C_{1-4}$ alkyl substituents, is oxidized to a compound of the formula

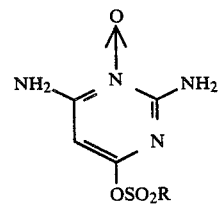

which according to known methods is reacted with piperidine to minoxidil. In the inventive method magnesium monoperoxyphthalate, which has the formula

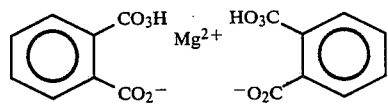

is used as the oxidizing agent.

3 Claims, No Drawings

METHOD FOR THE PREPARATION OF A THERAPEUTICALLY ACTIVE COMPOUND

This invention relates to a method for the preparation of 2,4-diamino-3-oxy-6-piperidylpyrimidine or minoxidil. Minoxidil, which has the formula

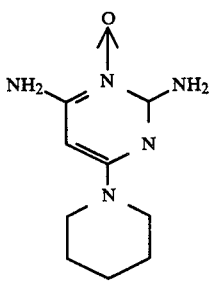

is useful as an antihypertensive agent.

Methods for the preparation of minoxidil have been disclosed for example in the German patent publication DOS No. 1620649, U.S. Pat. No. 3,910,928, Finnish Patent FI No. 55194 and Finnish Patent application No. 793307.

The Finnish patent application No. 793307 describes, e.g. a method for the preparation of minoxidil, where 6-hydroxy-2,4-diamino-pyrimidine is reacted with a sulfonyl halide of the formula R—$SO_2$-hal wherein hal is halogen, to a compound of the

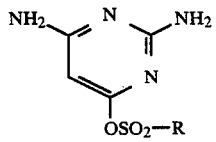

wherein R is a $C_{1-4}$ alkyl or a phenyl group optionally having up to three $C_{1-4}$ alkyl substituents.

This compound is then reacted with a peracid, for example m-chloroperbenzoic acid, to give a compound of the formula

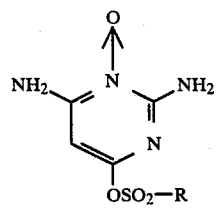

which finally is reacted with piperidine to give minoxidil.

The method described above has, however, some disadvantages. The oxidizing agent m-chloroperbenzoic acid or m-CPBA is a second grade poison. When oxidizing with this compound it is necessary to isolate the oxidation product according to a rather complicated and dangerous method: the solvent is evaporated to dryness, the residue is dissolved in a great amount of ethyl acetate, which is extracted several times with a dilute sodium hydroxide solution. Finally the ethyl acetate is dried and evaporated to a smaller volume whereon the product precipitates. Thus, when oxidizing with m-CPBA, the reaction mixture is evaporated to dryness and there is a risk that explosive peroxides are formed during the heating at dryness. In addition, oxidation with m-CPBA gives relatively large amounts of byproducts.

I have surprisingly found that the above mentioned disadvantages can be avoided if as the oxidizing agent instead of m-CPBA is used magnesium monoperoxyphthalate or MMPP, which has the formula

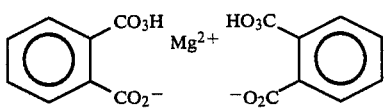

This compound is not classified as a toxic agent. It is a solid, a stable compound and is shock proof. When the oxidation is performed with this agent, the oxidation product can be precipitated directly from the aqueous solution.

Therefore complicated and dangerous distillation to dryness can be avoided. MMPP is a more reactive oxidant than m-CPBA, but still it does not result in byproducts to the same extent. Moreover, the use of MMPP is cheaper than m-CPBA. Hydrates of MMPP, such as the hexahydrate, can also be employed in the process of the present invention.

The method according to my invention can be described as follows:

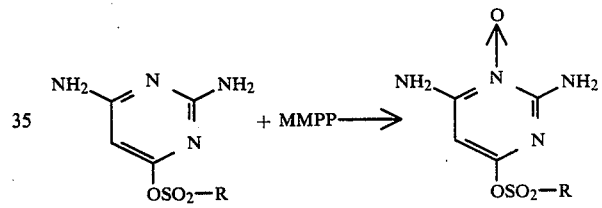

According to a preferred embodiment R is p-tolyl. The oxidation product then obtained, 6-tosyloxy-2,4-diaminopyrimidine-3-oxide, is further reacted according to known methods to minoxidil. The starting material, 6-(p-tolylsulfonyloxy)-2,4-diaminopyrimidine, can be prepared e.g. according to the method disclosed in FI application No. 793307.

The oxidation reaction can be performed in various solvents. Suitable solvents are for example alcohols, preferably lower alcohols, aqueous solutions of alcohols, acetic acid, acetone, tetrahydrofuran, aqueous solutions of methylene chloride and a phase transfer catalyst, DMF and DMSO. A suitable temperature ranges from 5° to 50° C., preferably 15°-30° C. The reaction can be performed in the pH range 4 to 9.

The method according to the invention is described in the following examples.

EXAMPLE (a) 2,4-diamino-3-oxy-6-(p-tolylsulfonyloxy)-pyrimidine 25 g (0.089 mol) of 2,4-diamino-6-(p-tolylsulfonyloxy)-pyrimidine prepared according to the method disclosed in FI application No. 793307 (example 1, step 1, method A), were suspended in a mixture containing 200 ml of acetone and 200 ml of water.

87.9 g (0.178 mol) of magnesium monoperoxyphthalate hexahydrate (MMPP) are added to this mixture. The mixture is stirred at room temperature for 4 hours.

250 ml of water are added and the mixture is stirred at a temperature of 5°–15° C. for 1 hr. The precipitate is filtered off and washed twice with 100 ml of water and once with 25 ml of cold methanol. 21 g (80%) of 2,4-diamino-3-oxy-6-(p-tolylsulfonyloxy)-pyrimidine are obtained. M.p. 128°–129° C. (decomposes).

(b) 2,4-diamino-3-oxy-6-piperidylpyrimidine 20 g (0.067 mol) of 2,4-diamino-3-oxy-6-(p-tolylsulfonyloxy)-pyrimidine from the foregoing step and 140 ml of piperidine are heated at 80°–90° C. for 2 hr. Piperidine is distilled off in vacuum. To the residue are added 50 ml of a 5% solution of sodium hydroxide in water and 50 ml of toluene, and the mixture is stirred at 20°–25° C. for half an hour. The mixture is filtered and the precipitate is washed twice with 30 ml of water and once with 30 ml of toluene. 8.4 g (60%) of 2,4-diamino-3-oxy-6-piperidylpyrimidine are obtained. M.p. 255°–260° C. (decomposes).

I claim:

1. A method for the preparation of 2,4-diamino-3-oxy-6-piperidylpyrimidine or minoxidil comprising the oxidation of a compound of the formula (I)

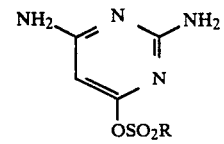

wherein R is a $C_{1-4}$ alkyl or a phenyl group to a compound of the formula (II)

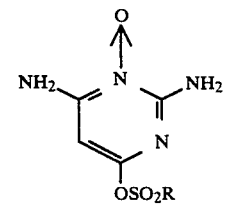

wherein the oxidizing agent is magnesium monoperoxyphthalate which has the formula (III)

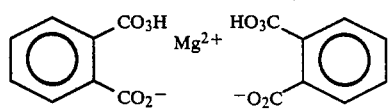

, and reacting the compound of the formula (II) with piperidine to obtain minoxidil.

2. A method according to claim 1 wherein R is p-tolyl.

3. A method according to claim 1 wherein R is a phenyl group having one to three $C_{1-4}$ alkyl substituents.